United States Patent [19]
Gilman et al.

[11] 4,153,799
[45] May 8, 1979

[54] PYRAZOL-1-YL BENZODIAZEPINES AND OXIMES THEREOF

[75] Inventors: Norman Gilman, Wayne; Rodney I. Fryer, North Caldwell, both of N.J.

[73] Assignee: Hoffmann-La Roche Inc., Nutley, N.J.

[21] Appl. No.: 942,210

[22] Filed: Sep. 14, 1978

Related U.S. Application Data

[62] Division of Ser. No. 775,346, Mar. 7, 1977, Pat. No. 4,130,716.

[51] Int. Cl.² ............................................. C07D 231/14
[52] U.S. Cl. ..................................................... 548/378
[58] Field of Search ................................. 548/378, 324

[56] References Cited
U.S. PATENT DOCUMENTS

| | | |
|---|---|---|
| 3,929,766 | 12/1975 | Metlesics ........................... 548/324 |
| 4,022,800 | 5/1977 | Gschwend ......................... 548/378 |
| 4,099,012 | 7/1978 | Gschwend ......................... 548/378 |

OTHER PUBLICATIONS

Heckendorn et al., Chem. Abst. 1976, vol. 84, No. 121844w.
Allgeier et al., Chem. Abst. 1976, vol. 84, No. 180231s.

*Primary Examiner*—John M. Ford
*Assistant Examiner*—Natalie Harkaway
*Attorney, Agent, or Firm*—Jon S. Saxe; Bernard S. Leon; Frank P. Hoffman

[57] ABSTRACT

Compounds are presented of the formula

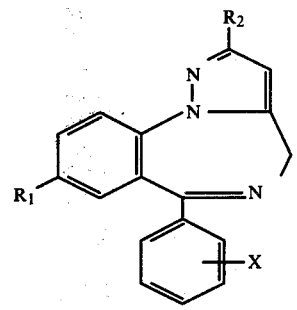

wherein $R_1$ is selected from the group consisting of hydrogen, amino, halogen and nitro; $R_2$ is selected from the group consisting of hydrogen, lower alkyl, carboxylic acids, esters and primary, secondary or tertiary amides thereof, alkylhydroxy, acylhydroxy-lower alkyl, amino-lower alkyl, alkylamino-lower alkyl, acylamino-lower alkyl and carboxaldehyde; and X is hydrogen or halogen and the pharmaceutically acceptable salts thereof.

Also presented are processes to produce the above compounds and intermediates thereof. These compounds exhibit pharmacological activity as anxiolytics, sedatives, muscle relaxants and anticonvulsants.

4 Claims, No Drawings

PYRAZOL-1-YL BENZODIAZEPINES AND OXIMES THEREOF

This is a division of application Ser. No. 775,346 filed Mar. 7, 1977, now U.S. Pat. No. 4,130,716.

BACKGROUND OF THE INVENTION

The present invention relates to compounds of the formula

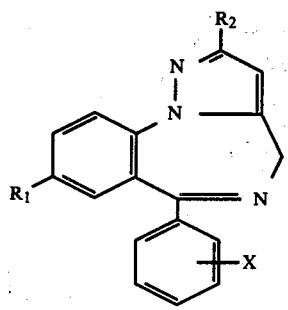

wherein $R_1$ is selected from the group consisting of hydrogen, amino, halogen and nitro; $R_2$ is selected from the group consisting of hydrogen, lower alkyl, carboxylic acids, esters and primary, secondary or tertiary amides thereof, alkylhydroxy, acylhydroxy-lower alkyl, amino-lower alkyl, alkylamino-lower alkyl, acylamino-lower alkyl and carboxaldehyde; and X is hydrogen or halogen and the pharmaceutically acceptable salts thereof.

As used in this disclosure, the term "lower alkyl" or "alkyl" comprehends both straight, cyclo and branched chain ($C_1$–$C_7$) carbon-hydrogen radicals, preferably $C_1$–$C_4$ carbon-hydrogen radicals such as methyl, ethyl, propyl, isopropyl, butyl and the like.

The term "halogen" is used to include all four forms thereof, i.e., chlorine, bromine, fluorine and iodine.

By the term "acyl" is meant a $C_1$ to $C_7$, preferably a $C_1$ to $C_4$, alkanoic acid moiety, i.e., radicals of the formula

wherein R is $C_1$–$C_6$ or hydrogen, e.g., acetyl, propionyl, butyryl and the like.

By the term "carboxylic acids and esters thereof" is meant moieties of the formula

wherein R is hydrogen or lower alkyl.

By the term "primary, secondary or tertiary amides of carboxylic acids" is meant moieties of the formula

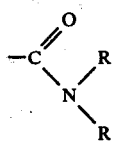

wherein R is either hydrogen or lower alkyl and may be the same or different.

By the term "acylhydroxy lower alkyl" is meant a moiety of the formula

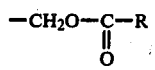

wherein R is lower alkyl.

By the terms "amino-lower alkyl", "acylamino-lower alkyl" and "alkylamino-lower alkyl" are meant a moiety of the formula

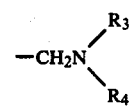

wherein $R_3$ and $R_4$ are hydrogen or $R_3$ is hydrogen and $R_4$ is acyl as defined above or lower alkyl or $R_3$ and $R_4$ are both alkyl.

The following reaction scheme sets forth the methods of preparation utilized to produce the novel compounds of the present invention.

Step 1

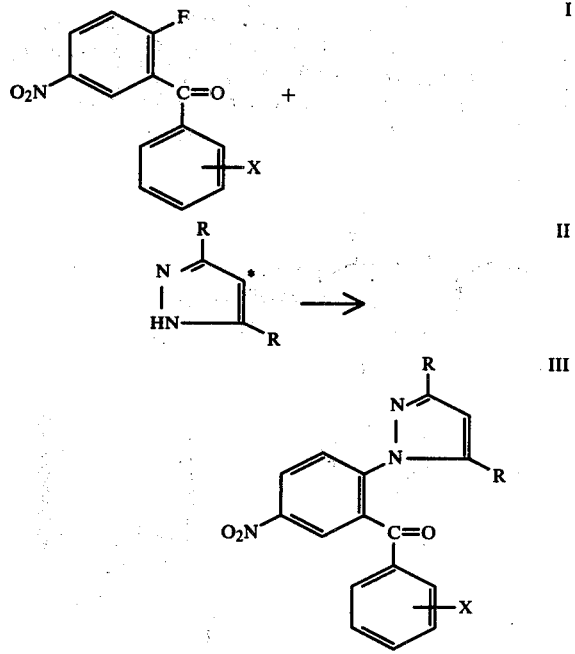

* J. Bastide and J. Lemarte, Bull. Soc. Chim. Fr., 1336 (1971)

wherein X is hydrogen or halogen and R is selected from the group consisting of $CO_2R_5$ and $CH_2OR_6$ wherein $R_5$ is lower alkyl and $R_6$ is acetyl.

The above reaction is carried out in the presence of an alkali metal hydride such as sodium or potassium hydride in a non-aqueous polar solvent such as dimethylformamide or dimethylsulfoxide. The reaction temperature may vary in the range of about 0° C. to 100° C. with a preferred range of 0° C. to 65° C.

Step 2

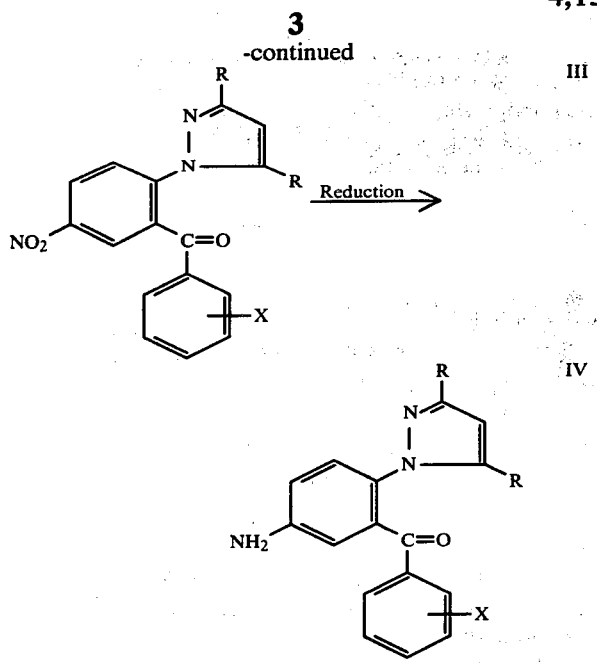

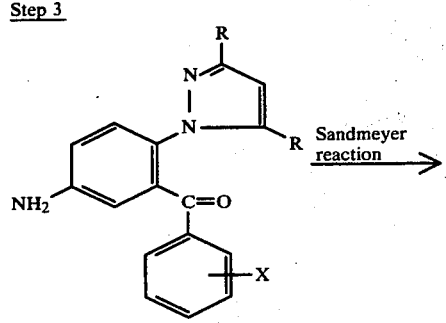

wherein X is as above and R is the group $CO_2R_5$ wherein $R_5$ is lower alkyl.

The above reduction of the nitro group to an amino group may be carried out by any suitable reducing agent but a preferred reducing agent would be stannous chloride dihydrate. Where one desires, any reducing agent that will selectively reduce a nitro group may be utilized. The solvent can be an aqueous acid. e.g., HCl, and the reaction carried out at a temperature range of 0° C.-100° C. with room temperature preferred.

Step 3

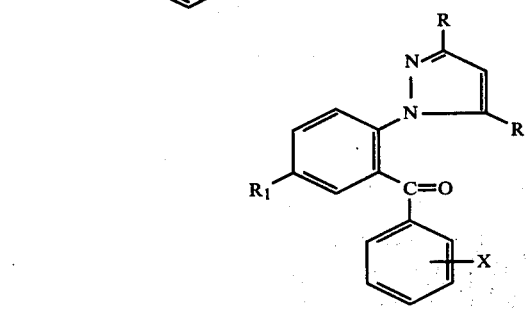

wherein R and X are as in Step 2 and $R_1$ is hydrogen or halogen.

The above reaction represents the well known "Sandmeyer reaction" wherein an amino group is replaced by different substituents, e.g., halogen (chloro, fluoro, bromo or iodo). The reactants utilized in the above "Sandmeyer reaction" are a mixture of sodium nitrite and cuprous chloride in hydrochloric acid which is utilized as a solvent to give the chloro substituent in this case. The other substituents may be arrived at by utilizing analogous reactants such as cuprous bromide, potassium iodide or fluoroboric acid. If desired, the amino group can also be replaced by hydrogen by means of reacting the diazonium salt with hypophosphorous acid.

Step 4

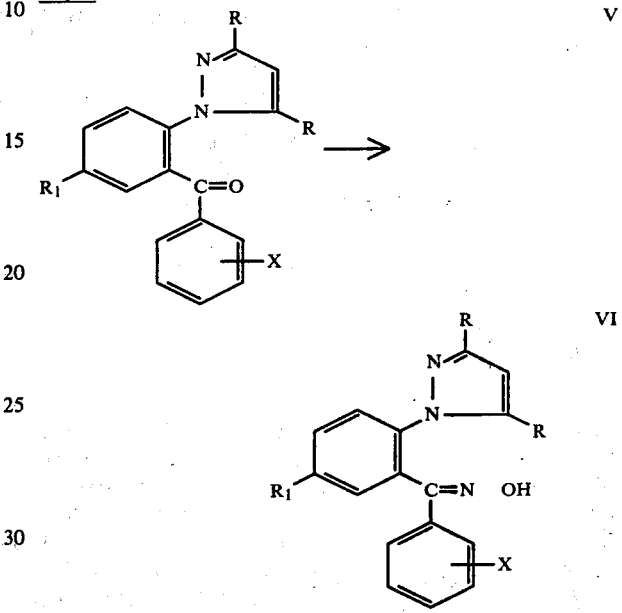

wherein R, $R_1$ and X are as in Step 3.

The above reaction represents the conversion of the benzophenone moiety to its oxime utilizing, e.g., hydroxylamine hydrochloride in a suitable inert solvent such as ethanol, or pyridine at reflux temperatures to room temperature, preferably at reflux. Utilization of such a process step is found in U.S. Patent 2,893,992 cited for reference.

Step 5

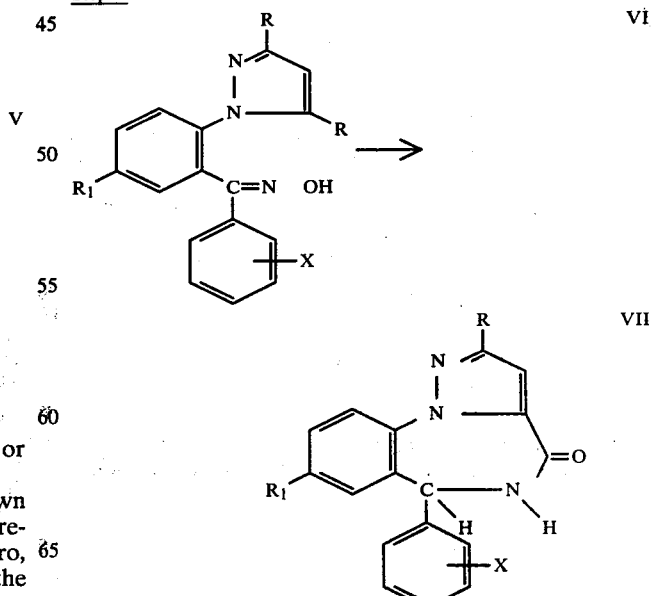

wherein R, R₁ and X are as in Step 3.

The above reaction represents a modified Clemmensen reduction to produce the desired lactam. To achieve the above end product a combination of zinc in acetic acid together with a catalytic amount of a mineral acid, e.g., hydrochloric acid, is utilized at about 25° C. to 100° C. with about 70° C. preferred.

Step 6

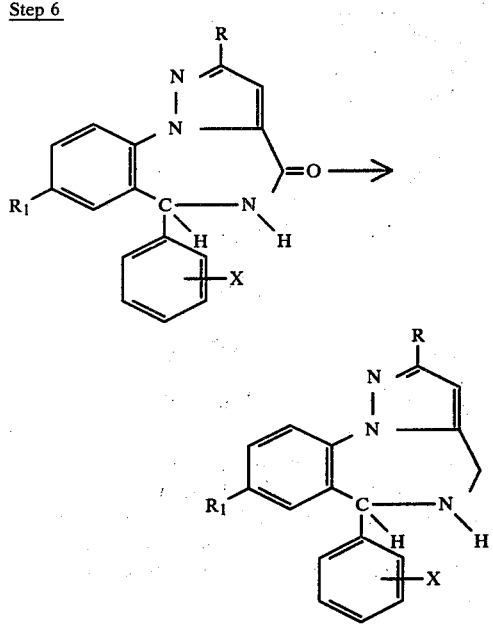

wherein R, R₁ and X are as in Step 3.

The above reaction represents a specific reduction step of the cyclic amide function. The reduction is carried out utilizing a borohydride reducing agent, e.g., diborane, at reflux temperature in an inert solvent such as tetrahydrofuran or long chain ethers, e.g., glyme and diglyme with THF preferred.

Step 7

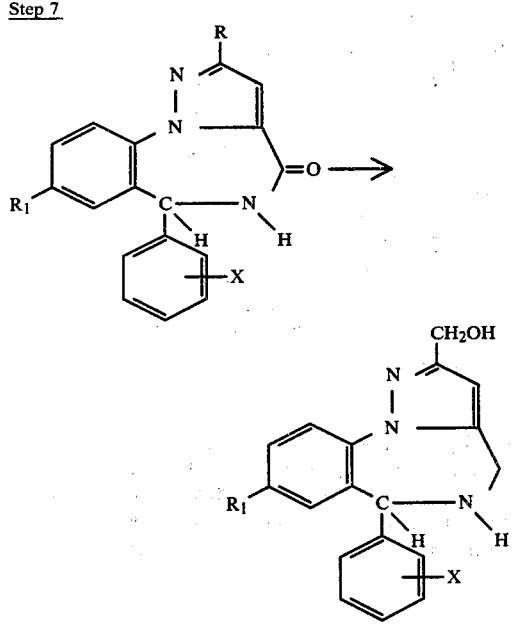

wherein R, R₁ and X are as in Step 5.

If desired, reduction of both the ester and amide functions can be carried out in one step utilizing a borohydride reducing agent, e.g., borane methyl sulfide, in an inert solvent such as the ethers alluded to in Step 6 at reflux temperatures to room temperatures with reflux preferred.

Step 8

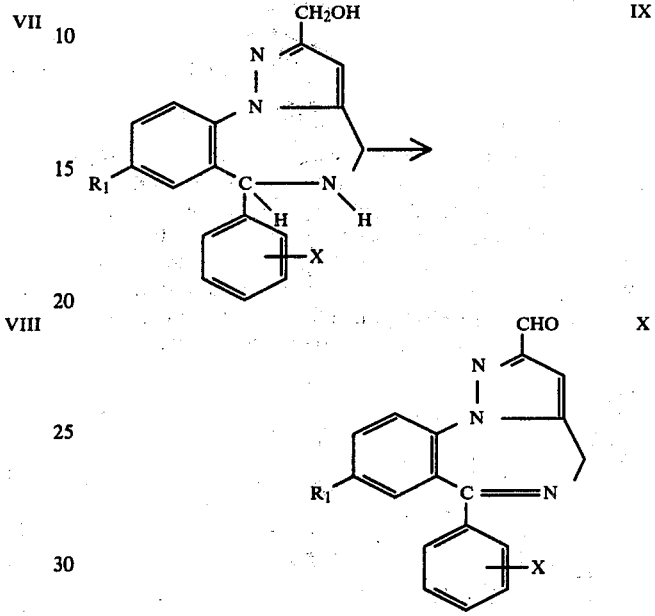

wherein X and R₁ are as in Step 5.

The above oxidation step of the amino alcohol to the aldehyde and of the amine to the imine is carried out utilizing manganese dioxide in the presence of an inert solvent such as tetrahydrofuran or methylene chloride at room temperature to reflux temperature with room temperature preferred.

Step 9

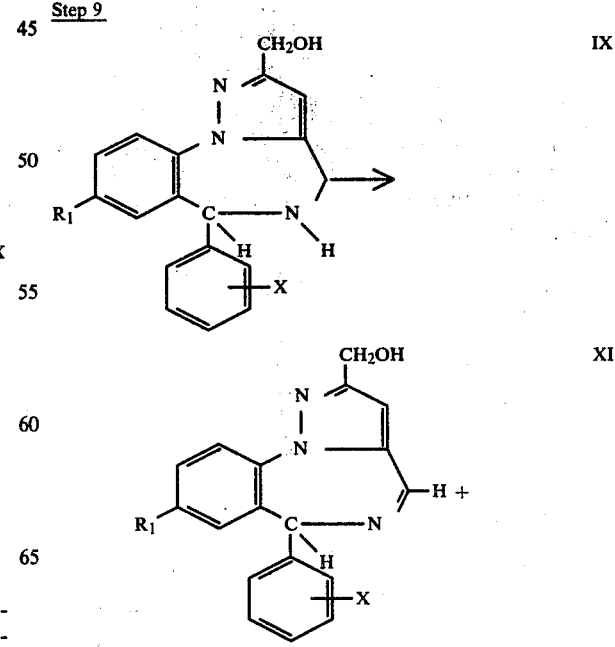

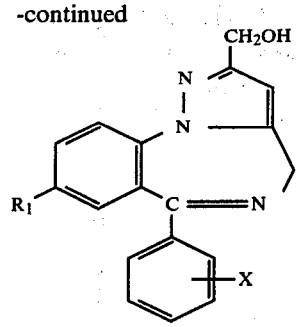

wherein $R_1$ and X are as in Step 5.

In the above reaction step the dihydrobenzodiazepine (IX) is oxidized with 2,3-dichloro-5,6-dicyano-1,4-benzoquinone (DDQ) in any inert solvent such as benzene or toluene at about reflux temperature to yield the desired benzodiazepine (XII) and minor amounts of the isomeric 6H benzodiazepine (XI) which may be removed by chromatography or recrystallization.

Step 10

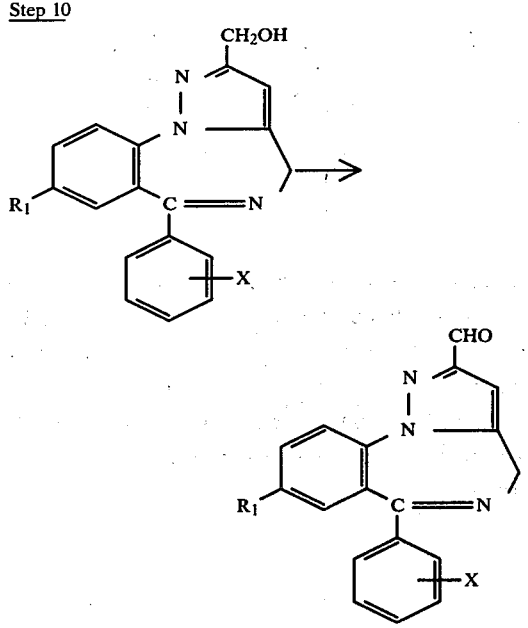

wherein X and $R_1$ are as in Step 5.

The above reaction step consists of the oxidation of the compound of formula XII with manganese dioxide utilizing the solvents and temperature ranges set forth in Step 8.

Step 11

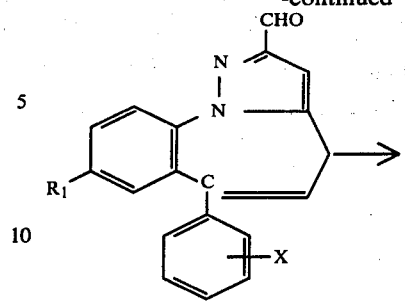

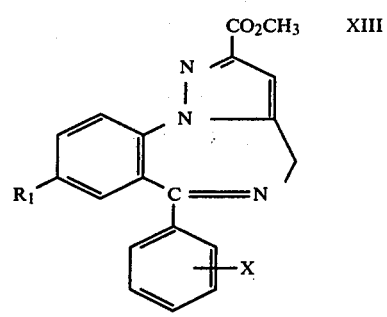

wherein X and $R_1$ are as in Step 5.

In the above reaction step the aldehyde (X) is reacted with an alcohol, e.g., a methanolic or ethanolic solution of sodium cyanide and the resulting acylcyanide oxidized in situ with manganese dioxide to the desired ester (XIII).

Step 12

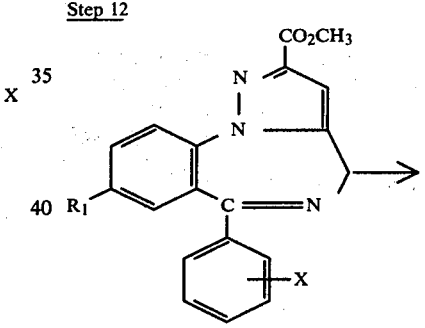

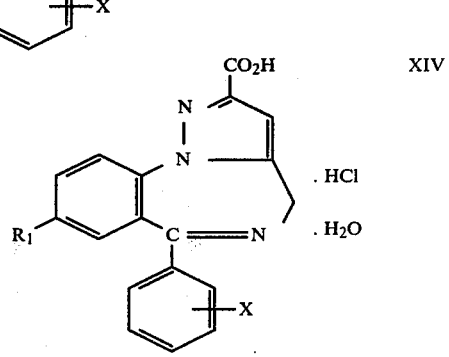

wherein $R_1$ and X are as in Step 5.

The ester function in compounds of the formula XIII may then be hydrolyzed by refluxing in a dilute mineral acid, e.g., dilute hydrochloric acid, to produce the corresponding carboxylic acid derivative (XIV).

Step 13

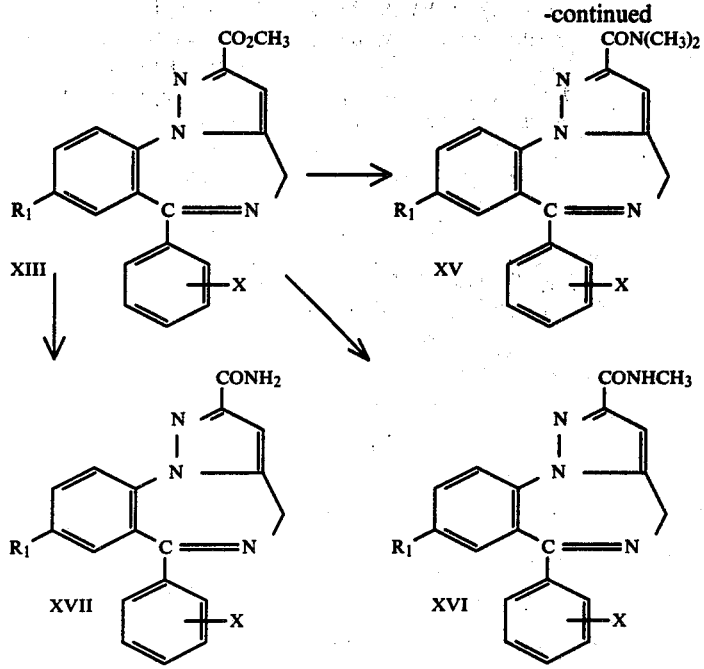

wherein $R_1$ and X are as in Step 5.

Compounds of the formula XIII may thereafter be converted to primary, secondary or tertiary amides (XVII, XVI and XV, respectively) by reaction with primary, secondary or tertiary amines in the presence of a lower alkanol, e.g., ammonia, monomethylamine, diethylamine, etc., in methanol, ethanol, etc., at from room temperature to reflux temperature, preferably at the reflux temperature of the solvent.

Step 14

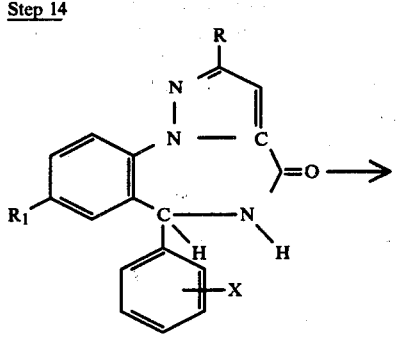

wherein R, $R_1$ and X are as in Step 5.

Compounds of the formula VI are reacted with a borohydride reducing agent e.g., sodium borohydride, in an inert solvent such as an alkanol, e.g., ethanol or an ether, e.g., tetrahydrofuran, to produce the reduced alcohol. The reaction is carried out at room tempera-ture to reflux temperature with reflux temperature preferred.

Step 15

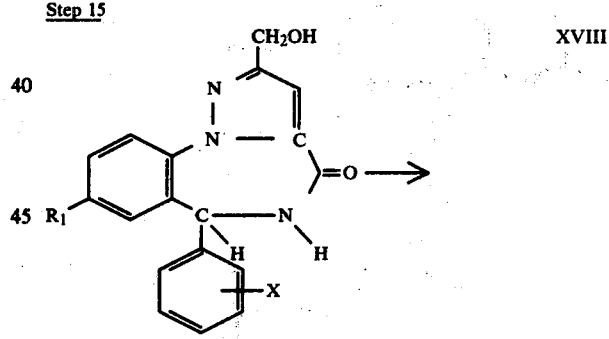

wherein $R_1$ and X are as in Step 5.

Compounds of the formula XVIII are thereafter oxidized with manganese dioxide utilizing the solvents and temperature ranges of Step 8, to the aldehyde (XIX).

Step 16

-continued

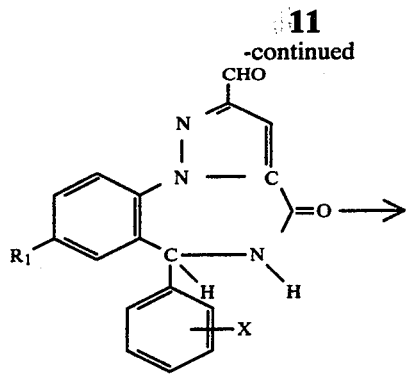
XIX

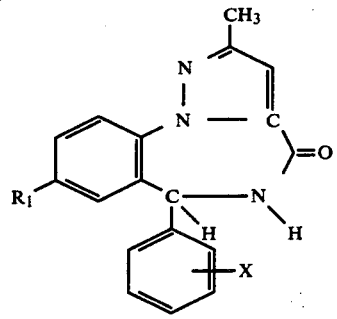
XX wherein $R_1$ and X are as in Step 5.

Compounds of the formula XIX thereafter undergo a Wolff-Kishner reduction, i.e., treatment of the aldehyde (XIX) with hydrazine hydrate or free hydrazine in a lower alkanol, e.g., methanol, ethanol, etc., followed by treatment with an alkali metal hydroxide such as potassium t-butoxide utilizing an inert solvent such as toluene, benzene, xylene, etc.

Step 17

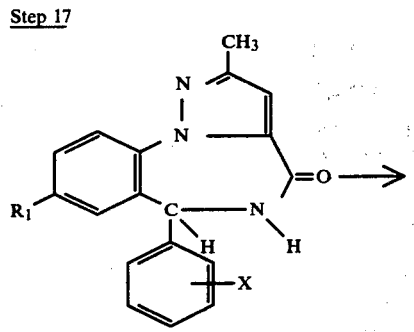
XX

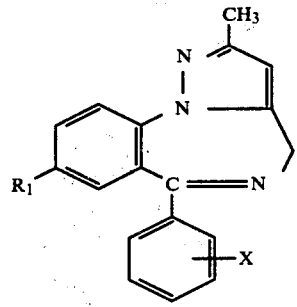
XXI wherein $R_1$ and X are as in Step 5.

The compound of the formula XX is initially reacted with a borohydride reducing agent, e.g., borane methyl sulfide, at temperature ranges and utilizing solvents as set forth in Step 7. After reduction of the amide compound is complete, the reaction mixture is thereafter oxidized utilizing 2,3-dichloro-5,6-dicyano-1,4-benzoquinone (DDQ) as the oxidizing agent utilizing sol- vents and temperature ranges as disclosed in Step 9 above.

The end products such as compounds X, XII, XIII, XIV, XV, XVI, XVII, XX wherein $R_1$ is amino can, if desired, be converted to the end products wherein $R_1$ is nitro by means of a Sandmeyer reaction. Other methods for the preparation of pyrazolobenzodiazepines wherein $R_1$ is nitro are set forth below.

Step 18

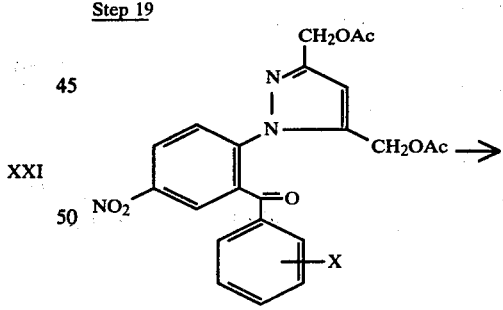

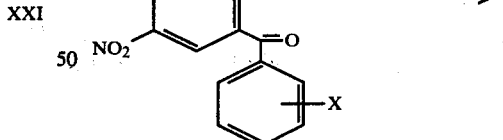
XXII wherein X is as in Step 5.

The above reaction step consists of the nucleophilic displacement reaction of the fluorobenzophenone with the pyrazolodiacetate utilizing the reactants, solvents and temperature ranges as set forth in Step 1 above.

Step 19

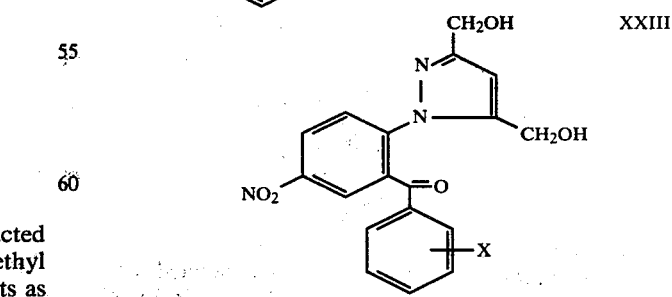
XXII

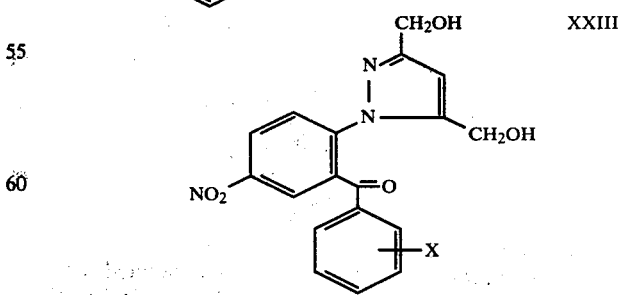
XXIII wherein X is as in Step 5.

The crude diacetate (XXII) is hydrolyzed directly with an aqueous mineral acid such as HCl to give the dialcohol compound (XXIII). The reaction is preferably carried out at reflux temperature but a range of room temperature to reflux temperature can be utilized.

Step 20

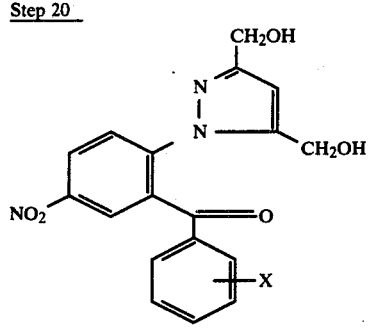

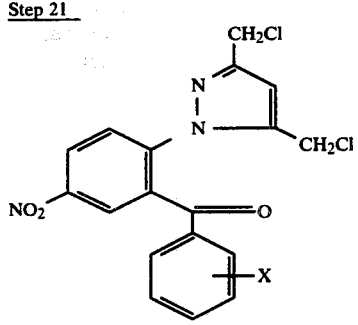

wherein X is as in Step 5.

The dialcohol compound (XXIII) is converted to the dichloro compound (XXIV) by reaction of compound XXIII with thionyl chloride at 40° C. to reflux temperature with reflux preferred.

Step 21

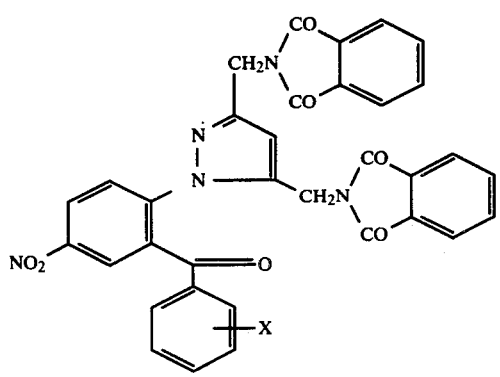

wherein X is as in Step 5.

Thereafter the dichloro compound undergoes a nucleophilic displacement by reaction with an alkali metal phthalimide, e.g., potassium, in an inert solvent such as dimethylformamide or dimethylsulfoxide at a temperature of 0° C. to 100° C., preferably at 65° C., to provide the diphthalimido product (XXV).

Step 22

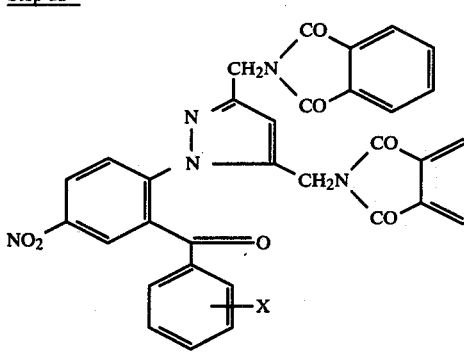

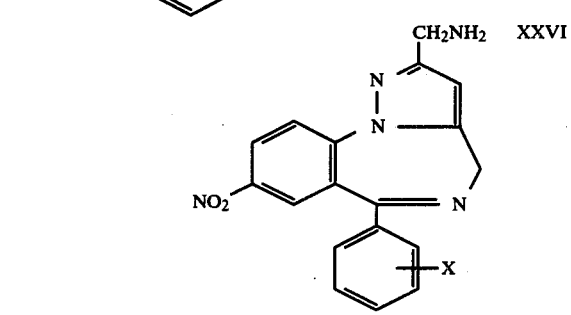

wherein X is as in Step 5.

The compound of the formula XXV is thereafter reacted in an alcoholic solution, e.g., methanol or ethanol, with an excess of hydrazine, e.g., hydrazine hydrate, at reflux temperatures to provide the cyclized amino compound (XXVI).

Step 23

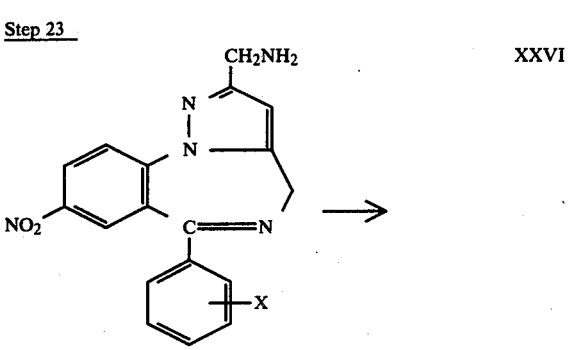

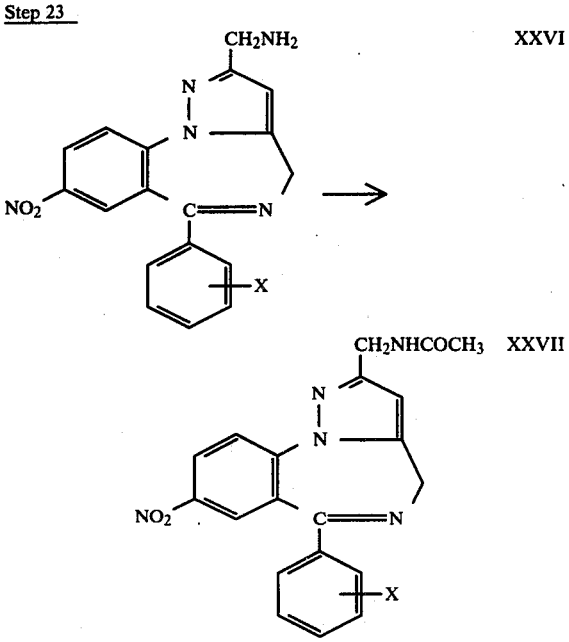

wherein X is as in Step 5.

The above reaction is accomplished by treatment of the amino compound (XXVI) with an acetylating agent, e.g., acetic anhydride, in situ in an inert solvent to provide the amide (XXVII). If desired, XXVII can be alkylated with an alkyl halide after first forming the alkali metal salt of the amide. Examples of such alkylation are well known in the art. Further, the acyl group can be hydrolyzed to yield the alkylaminoalkyl group which can be alkylated to the dialkylaminoalkyl group.

Step 24

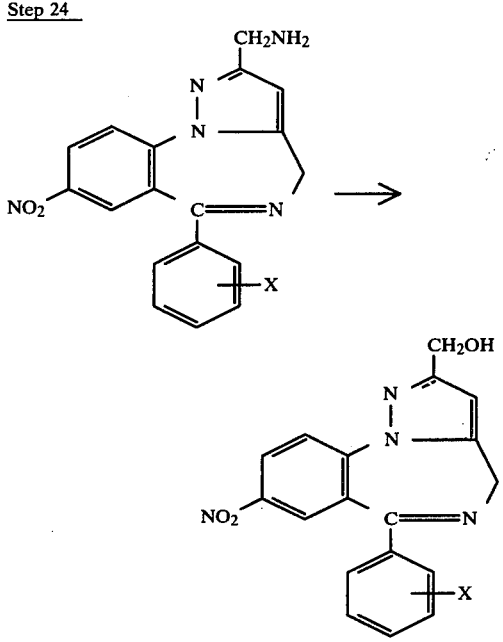

wherein X is as in Step 5.

The above reaction is carried out by diazotization of the amide (XXVI) in a solvent such as an aqueous acid, e.g., a mixture of acetic acid and water. The diazotization reaction is carried out utilizing sodium nitrite in water at a temperature range of 0° C. to 20° C. preferably at 10° C.

Step 25

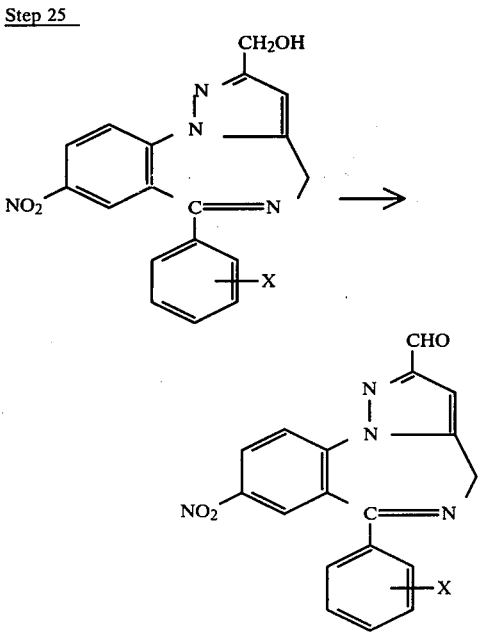

wherein X is as in Step 5.

The alcohol (XXVII) is thereafter oxidized to the aldehyde (XXVIII) following conditions set forth in Step 15 above.

Step 26

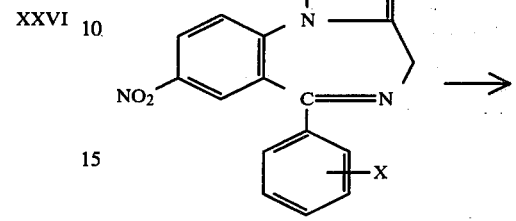

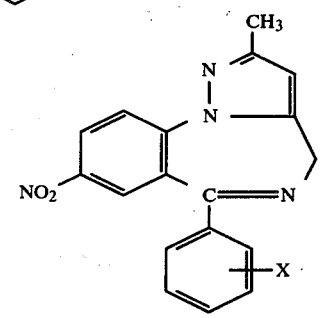

wherein X is as in Step 5.

The aldehyde (XXVIII) undergoes a Wolff-Kishner reduction as set forth in Step 16 above.

The compounds of the present invention exhibit pharmacological activity as anxiolytics, sedatives, muscle relaxants and anticonvulsants. As contemplated by this invention, the novel compounds of the present invention and their pharmaceutically acceptable salts can be embodied in pharmaceutical dosage formulations containing from about 0.1 to about 40 mg., most preferably 1–40 mg., with the dosage adjusted to species and individual patient requirements. The novel compounds and their pharmaceutically acceptable salts can be administered internally, for example, parenterally or enterally, in conventional pharmaceutical dosage forms. For example, they can be incorporated in conventional liquid or solid vehicles such as water, gelatin, starch, magnesium stearate, talc, vegetable oils and the like to provide talbets, elixirs, capsules, solutions, emulsions and the like according to acceptable pharmaceutical practices.

Preferred species of the compounds of the present invention are those of the formula

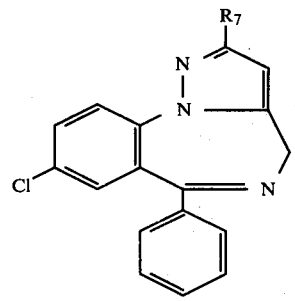

wherein $R^7$ is CONHCH$_3$, CONH$_2$ or CON(CH$_3$)$_2$ and the formula

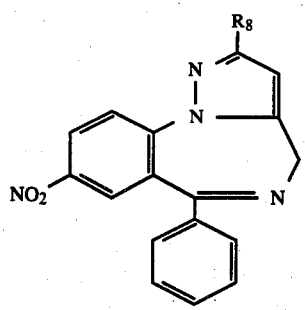

wherein R8 is CH2OH, CH2NH2 and CH2NHCOCH3.

The expression "pharmaceutically acceptable salts" is used to include both inorganic and organic pharmaceutically acceptable acids such as hydrochloric acid, hydrobromic acid, nitric acid, sulfuric acid, phosphoric acid, citric acid, formic acid, maleic acid, acetic acid, succinic acid, tartaric acid, methanesulfonic acid, para-toluenesulfonic acid and the like. Such salts can be formed quite readily by those skilled in the art, with the prior art and the nature of the compound to be placed in salt form, in view.

The following examples are meant to illustrate the invention but should not be viewed as limiting the scope thereof.

EXAMPLE 1

1-(2-Benzoyl-4-nitrophenyl)-3,5-pyrazole dicarboxylic acid dimethyl ester

To a slurry of 5.3 g. (110 mmol) of 50% NaH in mineral oil in 425 ml. of dry DMF, stirred at 3° under argon, was added portionwise over a 20 minute time period, 20.26 g. (110 mmol) of 3,5-pyrazole dicarboxylic acid dimethyl ester*, maintaining a temperature of 5°–8°. When the vigorous hydrogen evolution had stopped, the ice bath was removed and the reaction allowed to warm to room temperature while stirring for 20 minutes. A solution of 24.5 g. (100 mmol) of 2-fluoro-5-nitrobenzophenone, in 100 ml. of dry DMF was added dropwise over 40 minutes and when addition was complete, the reaction was heated at 65° for 1.5 hr. After cooling, the mixture was poured over a mixture of ice and brine and extracted well with a 1:1 EtOAc:ether mixture. The combined extracts were washed with brine, dried over MgSO4 and concentrated. The crude mixture was chromatographed on silica gel using as an eluent benzene mixed with 0–100% EtOAc. The residue remaining after the solvents were evaporated was recrystallized from EtOAc/hexane to give the final product. The analytical sample was prepared by an additional recrystallization from EtOAc/hexane and was obtained as off-white needles: mp 150°–152°.

*J. Bastide and J. Lemarte, Bull. Soc. Chim. Fr., 1336 (1971)

EXAMPLE 2

1-(2-Benzoyl-4-aminophenyl)-3,5-pyrazole dicarboxylic acid, dimethyl ester

A solution of 33.0 g. (150 mmol) of stannous chloride dihydrate in 65 ml. of 6N HCl and 200 ml. HOAc was added to a warm solution of 17.5 g. (42.7 mmol) of the product of Example 1 in 225 ml. HOAc. After cooling to room temperature while stirring for 16 hours, the reaction was poured into an ice-water slurry and made very basic (pH>13) with NaOH pellets, keeping the temperature of the mixture below 20° with extra additions of ice. The basic mixture was extracted thoroughly with CH2Cl2. The combined extracts were washed with brine, dried (Na2SO4) and concentrated in vacuo to give the final product. Recrystallization from methylene chloride/hexane gave an analytical sample as pale yellow needles: mp 171°–172°.

EXAMPLE 3

1-(2-Benzoyl-4-chlorophenyl)-3,5-pyrazole dicarboxylic acid, dimethyl ester

To a solution of 13.1 g. (34.5 mmol) of the final product of Example 2 in 50 ml. HOAc and 75 ml. of 3N HCl, stirred at 3°, was added dropwise so as to maintain a temperature of 3°–6°, a solution of 2.50 g. (36.3 mmol) of sodium nitrite in 25 ml. H2O. When the addition was complete, the reaction was stirred at 3° for 20 minutes. A fresh solution of cuprous chloride in concentrated hydrochloric acid (prepared from 27 g. cupric sulfate pentahydrate*) was mixed with an equal volume of water and cooled to 3°. The diazotized solution, which had to be kept cold (<5°) at all times, was slowly poured into the vigorously stirred 5° cuprous chloride solution in several portions, in order to control foaming. When addition was complete, the reaction was stirred for one hour while slowly warming to room temperature, then heated on a steam bath to an internal temperature of 95°. After cooling to room temperature, the reaction was made basic with NH4OH and extracted well with CH2Cl2. The combined extracts were washed with brine, dried (Na2SO4) and concentrated in vacuo to a brown oil. This crude product was chromatographed on silica gel using a 2% EtOAc in benzene solution as eluent to give the final product. An analytical sample was prepared by recrystallization from ether/hexane and was obtained as colorless crystals: mp 118°–120°.

*L. F. Feiser, "Organic Experiments", D. C. Heath and Company, Boston, 1964, pp. 237–238.

EXAMPLE 4

1-[4-Chloro-2-(alpha-hydroxyiminobenzyl)pentyl]-3,5-pyrazole dicarboxylic acid, dimethyl ester A mixture of 11.2 g. (28 mmol) of the final product of Example 3, 5.80 g. (84 mmol) of hydroxylamine hydrochloride and 180 ml. pyridine was heated to reflux for 6.5 hours. After cooling to room temperature, the reaction was concentrated in vacuo to remove the pyridine. The crude product, as isolated, was then chromatographed on silica gel, using 10% EtOAc in benzene as eluent, to give the final product. Recrystallization from EtOH/H2O gave an analytical sample as colorless prisms mp: 177°–179°.

EXAMPLE 5

7-Chloro-4-hydroxy-5-phenylpyrazolo[1,5-a]quinoline-2-carboxylic acid, methyl ester (side product) and 8-Chloro-5,6-dihydro-4-oxo-6-phenyl-4H-pyrazolo-[1,5-a][1,4]benzodiazepine-2-carboxylic acid, methyl ester (final product)

To a mixture of 13.6 g. (33 mmol) of the final product of Example 4, 10.7 g. (165 mmol) of zinc dust and 85 ml. HOAc, was added 1 ml. concentrated hydrochloric acid. The reaction mixture was then heated in a 70° oil bath for 5.75 hours, cooled to room temperature and filtered through hyflo. The collected solids were washed thoroughly with CH2Cl2 and the combined filtrate and washings concentrated in vacuo. The residue was cautiously neutralized and made basic with saturated sodium carbonate solution; sodium ethylenediaminetetraacetate was added to complex the zinc salts and the mixture was extracted well with $CH_2Cl_2$. The combined extracts were washed with saturated sodium bicarbonate solution, then with brine, dried ($Na_2SO_4$) and concentrated. The residue was triturated with acetone to give 8-chloro-5,6-dihydro-4-oxo-6-phenyl-4H-pyrazolo-[1,5-a][1,4]benzodiazepine-2-carboxylic acid, methyl ester. The concentrated mother liquor was chromatographed on a 63×2.5 cm. column of silica gel packed in benzene, using benzene containing gradually increasing amounts of ethyl acetate (5–40%) as eluent. The side product, 7-chloro-4-hydroxy-5-phenyl-pyrazolo[1,5-a]quinoline-2-carboxylic acid, methyl ester, was eluted first and then the desired final product was obtained. A small amount of side product was recrystallized from acetone/hexane to give an analytical sample as colorless needles: mp 236.5°–238°. An analytical sample of the final product was prepared by recrystallization from acetone/hexane and was obtained as colorless crystals: mp 222°–224°.

EXAMPLE 6

8-Chloro-5,6-dihydro-6-phenyl-4H-pyrazolo[1,5-a][1,4]benzodiazepine-2-carboxylic acid methyl ester (side product) and
8-Chloro-5,6-dihydro-6-phenyl-4H-pyrazolo[1,5-a][1,4]benzodiazepine-2-methanol (final product)

Method A

To a solution of 6.72 g. (18.3 mmol) of the final product of Example 5 in 190 ml. dry THF cooled to 3° under argon, was added dropwise 91.5 ml. of a 1M diborane solution (91.5 mmol), maintaining a temperature of less than 5°. When addition was complete, the reaction was stirred at 3°–5° for 10 minutes. After slowly warming to room temperature, the reaction was heated to reflux for 16 hours, then cooled to 5° and 40 ml. of 3N HCl was added dropwise to quench the reaction. The acidic reaction mixture was stirred 40 minutes at room temperature, then made basic with ice and 3N NaOH and extracted well with $CH_2Cl_2$. The combined extracts were dried over $Na_2SO_4$ and concentrated to give a foamy white solid. This crude product was chromatographed on a 63×3.5 cm. column of silica gel packed in benzene, using benzene containing 0–100% EtOAc as eluent. The partially reduced side product was eluted first and then the more polar end product.

A small amount of the side product was recrystallized from acetone/ether/hexane to give an analytical sample as colorless crystals: mp 160°–161°.

A small amount of the final product was recrystallized twice from acetone/hexane to give an analytical sample as colorless needles: mp 117°–119°.

Method B

To a solution of 12.1 g. (32.9 mmol) of the final product of Example 5 in 310 ml. dry THF under argon, was added dropwise via syringe over a 15 minute time period, 13.1 ml. (131 mmol) of borane methyl sulfide (BMS). The reaction was stirred at room temperature for 1 hour 15 minutes. After replacing the argon supply with a drying tube, the reaction was heated to reflux for 19 hours. A tlc analysis done at that time indicated no starting material remained, nor was any of the side product present. Methanol (150 ml) was added dropwise (very slowly at first, 15 minutes for the first 5 ml), to quench the reaction, keeping the temperature below 30°. When the addition was complete, the reaction was stirred 2 hours at room temperature, cooled to 5° and dry HCl gas bubbled into the reaction (keeping the temperature below 10°) until a pH of <2 was reached. The acidic solution was heated to reflux for 2.5 hours, cooled and concentrated in vacuo. The residue was taken up in $CH_3OH$ (500 ml.) and reconcentrated to dryness. The residue was mixed with ice, $CH_2Cl_2$ and 3N NaOH. The two-phases were separated and the aqueous phase extracted well with $CH_2Cl_2$. The combined organic phases were washed with brine, dried ($Na_2SO_4$) and concentrated in vacuo to give semipure end product which by tlc analysis (comparison with authentic sample) was shown to be greater than 80% pure). This crude product was then used as isolated in the DDQ oxidation.

EXAMPLE 7

8-Chloro-6-phenyl-4H-pyrazolo[1,5-a][1,4]benzodiazepine-2-carboxaldehyde

To a solution 400 mg. (1.23 mmol) of the final product of Example 8 in 40 ml. $CH_2Cl_2$, was added 1.60 g. of $MnO_2$. The mixture was stirred for 1¾ hours at 5°, then warmed to room temperature with stirring for 1 hour. After being stored at 10° for 68 hours, the mixture was warmed to room temperature and filtered through hyflo. The collected solids were washed thoroughly with $CH_2Cl_2$ and the combined filtrate and washings concentrated in vacuo. The residue was taken up in 40 ml. $CH_2Cl_2$ and a fresh 1.6 g. $MnO_2$ added. After stirring ½ hour at room temperature, a tlc indicated no starting material remained. The reaction was worked up as described above to give a foamy yellow solid, which by tlc analysis was a very complex mixture. Chromatography of the crude product on a 26×2.0 cm column of silica gel packed in benzene, using 4% EtOAc in benzene as the eluent yielded the final product. An analytical sample was prepared by recrystallization from acetone/hexane and was obtained as light yellow needles: mp 170°–172°.

EXAMPLE 8

8-Chloro-6-phenyl-6H-pyrazolo[1,5-a][1,4]benzodiazepine-2-methanol (side product) and
8-Chloro-6-phenyl-4H-pyrazolo[1,5-a][1,4]benzodiazepine-2-methanol (end product)

A solution of 8.96 g. (39.5 mmol) of 2,3-dichloro-5,6-dicyano-1,4-benzoquinone (DDQ) in 450 ml. benzene was added dropwise to a solution of 11.8 g. (>26.3 mmol) of semipure end product of Example 6 (from the BMS reduction) in 325 ml. benzene. When addition was complete, the dark green solution was heated to reflux for 30 minutes to yield an orange mixture. After cooling to room temperature the mixture was filtered and the collected solids washed thoroughly with benzene. The combined filtrate and washings were concentrated in vacuo and the residue taken up in EtOAc and washed twice with water. The organic phase was then extracted six times with 3N HCl and the combined acidic phases were washed with EtOAc and then made basic. The basic solution was extracted four times with methylene chloride and the combined extracts washed with brine, dried ($Na_2SO_4$) and concentrated in vacuo. The crude product was chromatographed on a 21×5.5 cm column of silica gel packed in benzene, using 25% EtOAc in benzene solution to elute the unwanted isomer (side product) and EtOAc to elute the desired isomer (end product).

The purification yielded the side product; an analytical sample was prepared by recrystallization from ether/hexane and obtained as colorless needles: mp 147°-149°.

The purification yielded the end product. An analytical sample was prepared by recrystallization from acetone/hexane and was obtained as colorless needles: mp 174°-176°.

EXAMPLE 9

8-Chloro-6-phenyl-4H-pyrazolo[1,5-a][1,4]benzodiazepine-2-carboxylic acid, methyl ester A mixture of 7.7 g. (23.8 mmol) of the end product of Example 8, 30.8 g. of activated manganese dioxide ($MnO_2$) and 850 ml. of $CH_2Cl_2$ was heated to reflux for 18 hours. After cooling to room temperature, the mixture was filtered through hyflo and the collected solids washed thoroughly with $CH_2Cl_2$. The combined filtrate and washings were concentrated in vacuo to give the aldehyde of Example 7. The analysis (comparison with an authentic sample) showed the material to be the desired aldehyde.

A solution of 5.03 g. (102.5 mmol) of sodium cyanide in 503 ml. methanol was added to the 6.6 g. (20.5 mmol) of the aldehyde with stirring; 35.6 g. (410 mmol) of $MnO_2$ was added to the reaction and the mixture stirred at room temperature for 6 hours. The mixture was filtered through hyflo and the collected solids washed thoroughly with $CH_2Cl_2$. The combined filtrates and washings were cautiously concentrated in vacuo using a 30° water bath. The residue was mixed with water and extracted well with $CH_2Cl_2$. The combined extracts were dried ($Na_2SO_4$) and concentrated in vacuo to give the crude product. Recrystallization from $CH_2Cl_2$/hexane yielded purified end product, mp 208°-210°. An analytical sample was prepared by recrystallization from acetone/hexane and obtained as light yellow needles: mp 209°-211°.

EXAMPLE 10

8-Chloro-6-phenyl-4H-pyrazolo[1,5-a][1,4]benzodiazepine-2-carboxylic acid hydrochloride monohydrate A mixture of 1.05 g. (3 mmol) of the end product of Example 9 in 3 ml. acetone and 30 ml. of 1N HCl was heated to reflux for 2 hours. After cooling to room temperature, the mixture was concentrated in vacuo and the residue recrystallized twice from $H_2O$/acetone/ether to give analytically pure end product as off-white prisms: mp 268°-269°.

EXAMPLE 11

8-Chloro-6-phenyl-4H-pyrazolo[1,5-a][1,4]benzodiazepine-2-carboxamide

A solution of 750 mg. (2.13 mmol) of the end product of Example 9 in 50 ml. methanol in a glass bomb was cooled to 3° and saturated with ammonia. The glass bomb was then sealed and the reaction heated to 70° with stirring, for 16 hours. After cooling to 5°, the bomb was opened, the contents transferred to a r.b. flask and concentrated in vacuo. Recrystallization from acetone/hexane yielded end product, mp 216°-218°. An analytical sample was prepared by an additional recrystallization from acetone/hexane and obtained as pale yellow needles: mp 217°-219°.

EXAMPLE 12

8-Chloro-N-methyl-6-phenyl-4H-pyrazolo[1,5-a][1,4]benzodiazepine-2-carboxamide

This compound was prepared from 1.48 g. (4.2 mmol) of the end product of Example 9 and mono-methylamine according to the procedure described above in Example 11. Recrystallization from acetone/ether/hexane gave the desired product, mp 170°-172°. An analytical sample was prepared by recrystallization from the same solvent system and isolated as colorless needles: mp 170°-172°.

EXAMPLE 13

8-Chloro-N,N-dimethyl-6-phenyl-4H-pyrazolo[1,5-a][1,4]benzodiazepine-2-carboxamide This compound was prepared from 700 mg. (1.99 mmol) of the end product of Example 9 and dimethylamine according to a procedure similar to that described above in Example 11. The reaction mixture was heated to 60°-65° in a sealed glass bomb for 16 hours. Recrystallization from acetone/ether/hexane yielded the desired end product: mp 176°-178°.

EXAMPLE 14

8-Chloro-5,6-dihydro-4-oxo-6-phenyl-4H-pyrazolo[1,5-a][1,4]benzodiazepine-2-methanol To a slurry of 4.63 g. (122.4 mmol) of sodium borohydride in 525 ml. dry THF under argon, was added 6.25 g. (17 mmol) of the end product of Example 5. The mixture was heated to reflux for 6 hours, then cooled to 5° and 160 ml. of 1N HCl added dropwise to hydrolyze the excess borohydride. When addition was complete, the mixture was concentrated in vacuo to remove the THF. The remaining aqueous phase was made basic (pH=8) with saturated sodium bicarbonate solution and extracted thoroughly with $CH_2Cl_2$. The combined extracts were dried ($Na_2SO_4$) and concentrated in vacuo to give the desired product. Two recrystallizations from acetone/hexane gave an analytical sample as a colorless solid: mp 260°-262°.

EXAMPLE 15

8-Chloro-5,6-dihydro-4-oxo-6-phenyl-4H-pyrazolo[1,5-a][1,4]benzodiazepine-2-carboxaldehyde A solution of 5.85 g. (17 mmol) of the end product of Example 14 in 600 ml. dry THF was mixed with 24 g. of activated $MnO_2$ and heated to reflux for 17 hours. The mixture was cooled, filtered and the collected solids washed thoroughly with THF. The combined filtrate and washings were concentrated in vacuo. Recrystallization of this crude product from THF/hexane yielded the desired end product. An analytical sample was prepared by an additional recrystallization from THF/hexane and was obtained as colorless plates: mp 276°-278°.

EXAMPLE 16

8-Chloro-2-methyl-5,6-dihydro-4-oxo-6-phenyl-4H-pyrazolo[1,5-a][1,4]benzodiazepine To a solution of 3.43 g. (10.15 mmol) of the end product of Example 15 in 60 ml. of absolute EtOH, was added 12 ml. of hydrazine-hydrate. The reaction was heated to reflux for 17 hours, then cooled and concentrated in vacuo. The residue was taken up in 60 ml. toluene; 1.0 g. potassium t-butoxide added and the mixture heated to reflux for 8 hours, then cooled to room temperature and stirred for 9 hours. The reaction was poured over ice and brine and toluene added. The toluene phase was separated and dried over $Na_2SO_4$. The aqueous phase was extracted well with $CH_2Cl_2$ and the combined extracts dried over $Na_2SO_4$. The dried solutions were combined and concentrated and the crude product recrystallized from THF/hexane to give the desired end product, mp 258°–261°. An analytical sample was prepared by an additional recrystallization from THF/hexane and was obtained as colorless crystals: mp 259°–261°.

EXAMPLE 17

8-Chloro-2-methyl-6-phenyl-4H-pyrazolo[1,5-a][1,4]benzodiazepine

A solution of 2.52 g. (7.8 mmol) of the end product of Example 16 in 75 ml. dry THF was reduced with 3.12 ml. (31.2 mmol) of BMS according to the procedure described above in 6, Method B. The crude product from this reduction was then treated with 2.15 g. (9.4 mmol) of DDQ according to the oxidation procedure described above in Example 8. The crude oxidation product was chromatographed on a 29×20 cm column of silica gel packed in benzene and eluted first with 3% EtOAc in benzene and then 5% EtOAc in benzene. Recrystallization from $CH_3OH/H_2O$ of the material isolated from the column yielded the analytically pure end product as colorless needles: mp 105°–107°.

EXAMPLE 18

1-Triphenylmethyl-3,5-pyrazoledicarboxylic acid, dimethyl ester

To a solution of 1.84 g. (10 mmol) of 3,5-pyrazoledicarboxylic acid dimethyl ester* in 15 ml. of DMF, stirred at 0° under argon, was added 480 mg. (10 mmol) of 50% NaH (suspension in mineral oil). After the evolution of hydrogen had ceased, 2.7 g. (10 mmol) of triphenylmethyl chloride in 20 ml. of DMF was added dropwise. The mixture was allowed to warm to room temperature, stirred 1.5 hours, poured into $H_2O$, and the resulting precipitate filtered. After recrystallization from 2-ethoxyethanol-$H_2O$, there was obtained the end product. The analytical sample was obtained as colorless needles by recrystallization from DMF-$H_2O$; mp 212°–213.5°.

*J. Bastide and J. Lemarte, *Bull. Soc. Chim. Fr.*, 1336 (1971).

EXAMPLE 19

1-Triphenylmethyl-3,5-dihydroxymethylpyrazole

A solution of 25 g. (59 mmol) of the end product of Example 18 in 800 ml. of THF was added dropwise to a slurry of 3.8 g. (100 mmol) of $LiAlH_4$ in 400 ml. of THF stirred at 0°. After warming to room temperature the mixture was refluxed for 1 hour, cooled, and the excess $LiAlH_4$ decomposed by the dropwise addition of $H_2O$, followed by 3N NaOH. The salts were filtered and washed with $CH_2Cl_2$. The filtrates were concentrated to give the end product as a white solid, mp 180°–182°. The analytical sample was obtained as colorless needles by recrystallization from $CH_3OH$-$H_2O$; mp 180°–182°.

EXAMPLE 20

1-Triphenylmethyl-3,5-diacetoxymethylpyrazole

A solution of 19.5 g. (0.053 mol) of the end product of Example 19, 90 ml. of acetic anhydride and 20 ml. of $Et_3N$ was stirred at room temperature for 2.5 hours. After pouring into 1N NaOH, the solution was extracted with $CH_2Cl_2$. The organic phase was dried ($MgSO_4$), concentrated and the residue recrystallized from $CH_3OH$ to give the end product. The analytical sample was prepared from the same solvent; colorless plates; mp 119°–121°.

EXAMPLE 21

3,5-Diacetoxymethylpyrazole

To a solution of 90 ml. of $CF_3CO_2H$ and 15 ml. of $H_2O$, cooled to −20° was added, in portions, 10 g. (0.022 mol) of the end product of Example 20. After the addition was complete, the solution was stirred at −15° to −20° for 1 hour, poured into excess saturated $K_2CO_3$ solution and extracted with EtOAc. The organic phase was dried ($MgSO_4$), concentrated and the residue chromatographed on silica gel to give the end product as a pale yellow oil. The analytical sample was obtained as a colorless oil by bulb to bulb distillation: bp 175 (0.05 mm).

EXAMPLE 22

[2-[3,5-bis(Acetoxymethyl)pyrazol-1-yl]-5-nitrophenyl]phenyl methanone

A solution of 4.2 g. (20 mmol) of 3,5-diacetoxymethylpyrazole in 15 ml. of DMF was added dropwise to a suspension of 960 mg. (20 mmol) of NaH (50% in mineral oil) in 25 ml. of DMF stirred at 0° and under argon. After the evolution of $H_2$ had ceased, 4.9 g. (20 mmol) of 2-fluoro-5-nitrobenzophenone was added in one portion. After stirring at 0° for 4 hours, the mixture was poured into ice-water and extracted with EtOAc. The organic phase was washed with dil. brine, dried ($MgSO_4$) and concentrated. The residue was chromatographed on silica gel using benzene/EtOAc (1:1) as eluent. Removal of the solvents gave crude end product as a gum which was not purified further. The nmr ($CDCl_3$) had signals at: δ2.00 (3H, s, $CH_3$), 2.07 (3H, s, $CH_3$), 4.82 (2H, s, $CH_2$), 5.10 (2H, s, $CH_2$) 6.33 (1H, s, C=CH), and 7.30–8.67 (8H, m, $C_6H_5+C_6H_3$).

EXAMPLE 23

[2-[3,5-bis(Hydroxymethyl)pyrazol-1-yl]-5-nitrophenyl]phenylmethanone

A solution of 5.6 g. (12.8 mmol) of the end product of Example 22 in 100 ml. of 3N HCl was refluxed for 3.5 hours. The solution was cooled, poured into excess saturated $K_2CO_3$ and extracted with EtOAc. The organics were washed with brine, dried ($MgSO_4$), concentrated and the residue chromatographed on silica gel with benzene/EtOAc (1:1) to give the end product as a pale yellow solid. An analytical sample was prepared by recrystallization from $CH_3OH$—$H_2O$; mp 145°–147°.

EXAMPLE 24

[2-[3,5-bis(Chloromethyl)pyrazol-1-yl]-5-nitrophenyl]-phenylmethanone

A solution of 2 g. (5.7 mmol) of the end product of Example 23 and 30 ml. of $SOCl_2$ was refluxed for 0.5 hour. The excess $SOCl_2$ was removed in vacuo and the residue partitioned with cold saturated $K_2CO_3$ and EtOAc. The EtOAc extracts were washed with brine, dried ($MgSO_4$) and concentrated to give the end product as a tan solid. The analytical sample was obtained as tan plates by recrystallization from EtOH; mp 152°–155°.

EXAMPLE 25

[2-[3,5-bis(Phthalimidomethyl)pyrazol-1-yl]-5-nitrophenyl]phenylmethanone

A mixture of 12.8 g. (32.8 mmol) of the end product of Example 24, 18.5 g. (100 mmol) of potassium phthalimide, and 250 ml. of DMF was stirred and heated at 65° for 18 hours. After cooling, the mixture was poured over ice, washed with dil. brine, dried ($MgSO_4$) and concentrated in vacuo. The residue was filtered through silica gel using EtOAc as an eluent. Removal of the solvent left the end product as a pale yellow solid, mp. 220°−224°. The analytical sample was prepared by recrystallization from acetone-hexane: pale yellow needles, mp 225°−226.5°.

EXAMPLE 26

2-Aminomethyl-8-Nitro-6-phenyl-4H-pyrazolo[1,5-a][1,4]benzodiazepine

A solution of 7.2 g. (11.8 mmol) of the end product of Example 25, 4 g. of $NH_2NH_2.H_2O$, and 350 ml. of EtOH was refluxed for 5 hours. A precipitate of phthalhydrazide began forming after ca. 1 hour. The solution was cooled, concentrated and the residue triturated with $EtOAc/CH_3OH$ (4:1). The phthalhydrazide was removed by filtration and washed with the above solvent mixture. The filtrates were concentrated and the residue triturated with $CH_2Cl_2$ and filtered. Removal of the $CH_2Cl_2$ in vacuo left crude end product as a gum which was not purified further.

EXAMPLE 27

2-Acetamidomethyl-8-nitro-6-phenyl-4H-pyrazolo[1,5-a][1,4]benzodiazepine

A mixture of 4 g. (12 mmol) of the end product of Example 26, 25 ml. of acetic anhydride and 5 ml. of triethylamine was stirred at room temperature for 1 hour. After pouring into ice water, the precipitate was filtered and washed with water to give the end product as a yellow-tan solid, mp 208°−211°. The analytical sample was obtained as tan plates by recrystallization from $EtOH-H_2O$; mp 211°−213°.

EXAMPLE 28

8-Nitro-6-phenyl-4H-pyrazolo[1,5-a][1,4]benzodiazepine 2-methanol

To a solution of 3.8 g. (11 mmol) of the end product of Example 26 in 30 ml. of HOAc and 6 ml. of $H_2O$, was added dropwise a solution of 1.1 g. (16 mmol) of $NaNO_2$ in 3 ml. of $H_2O$. After stirring for 1 hour, the solution was warmed on a steam bath, cooled and added to saturated $K_2CO_3$. The solid which was precipitated was filtered and chromatographed on silica gel using benzene-EtOAc (3:1) to elute 1.4 g. (24%) of the acetate of the end product. The acetate was non-crystalline and was characterized by nmr: δ2.10 (3H, s, $CH_3$), 4.67 (2H, bs, $CH_2$), 5.20 (2H, s, $CH_2O$), 6.43 (1H, s, C=CH), 7.43 (5H, s, $C_6H_5$) and 8.10–8.53 (3H, m, $C_6H_3$). The desired alcohol was eluted from the column using benzene/EtOAc (1:1). The analytical sample was obtained as faint yellow plates by recrystallization from $CH_3OH$; mp 192°−193.5°.

EXAMPLE 29

2-Fluoro-5-nitrobenzophene

A mixture of 162 g. (0.62 mol) of 2-chloro-5-nitrobenzophenone, 169 g. (2.9 mol) of anhydrous KF and 1.3 l. of DMF was stirred and refluxed overnight. After cooling, the mixture was poured over ice and extracted with ether. The organics were combined, washed well with dilute brine, dried and concentrated. The residue was filtered through silica gel using ether-hexane (1:1) as eluent. After removing the solvents, the residue was recrystallized from EtOH to give the product, m.p. 45°−47°.

EXAMPLE 30

| Wet Granulation Tablet Formulation | | | | |
|---|---|---|---|---|
| | mg/tablet | | | |
| 1. 8-nitro-6-phenyl-4H-pyrazolo [1,4-a]a 1,4]benzodiazepine 2-methanol | 1.0 | 5.0 | 10.0 | 50.0 |
| 2. Lactose | 195.0 | 230.0 | 264.0 | 263.0 |
| 3. Pregelatinized Starch | 12.5 | 15.0 | 17.5 | 20.0 |
| 4. Cornstarch | 25.0 | 30.0 | 35.0 | 40.0 |
| 5. Modified Starch | 12.5 | 15.0 | 17.5 | 20.0 |
| 6. Magnesium Stearate | 4.0 | 5.0 | 6.0 | 7.0 |
| Total | 250 mg | 300 mg | 350 mg | 400 mg |

Procedure:
1. Mix items 1–5 in a suitable mixer, granulate with water. Dry overnight in an oven. Mill through a Fitzpatrick mill.
2. Mix with item 6 and compress on a suitable press.

EXAMPLE 31

| Capsule Formulation | | | | |
|---|---|---|---|---|
| | mg/capsule | | | |
| 1. 8-nitro-6-phenyl-4H-pyrazolo [1,5-a] [1,4] benzodiazepine 2-methanol | 1.0 | 5.0 | 10.0 | 50.0 |
| 2. Lactose | 149.0 | 182.5 | 215.0 | 250.0 |
| 3. Cornstarch | 40.0 | 50.0 | 60.0 | 80.0 |
| 4. Magnesium Stearate | 2.0 | 2.5 | 3.0 | 4.0 |
| 5. Talc | 8.0 | 10.0 | 12.0 | 16.0 |
| Total | 200 mg | 250 mg | 300 mg | 400 mg |

Procedure:
1. Mix items 1–3 in a suitable mixer. Mill through suitable mill.
2. Mix with items 4 and 5 and fill on capsule machine.

EXAMPLE 32

| Direct Compression Tablet Formulation | | | | |
|---|---|---|---|---|
| | mg/tablet | | | |
| 1. 8-nitro-6-phenyl-4H-pyrazolo [1,5-a] [1,4] benzodiazepine 2-methanol | 1.0 | 5.0 | 10.0 | 50.0 |
| 2. Lactose, Anhydrous DTG | 127.0 | 142.5 | 182.0 | 206.0 |
| 3. Microcrystalline Cellulose | 40.0 | 50.0 | 60.0 | 80.0 |
| 4. Modified Starch | 10.0 | 12.5 | 15.0 | 20.0 |
| 5. Cornstarch | 20.0 | 25.0 | 30.0 | 40.0 |
| 6. Magnesium Stearate | 2.0 | 2.5 | 3.0 | 4.0 |

-continued

Direct Compression Tablet Formulation

| | mg/tablet | | | |
|---|---|---|---|---|
| Total | 200 mg | 250 mg | 300 mg | 400 mg |

Procedure:
1. Mix items 1-5 in a suitable mixer for 1 to 15 minutes.
2. Add item 6 and mix for 5 minutes. Compress on a suitable press.

EXAMPLE 33

Wet Granulation Tablet Formulation

| | mg/tablet | | | |
|---|---|---|---|---|
| 1. 8-chloro-2-methyl-6-phenyl-4H-pyrazolo [1,5-a] [1,4] benzodiazepine | 1.0 | 5.0 | 10.0 | 50.0 |
| 2. Lactose | 195.0 | 230.0 | 264.0 | 263.0 |
| 3. Pregelatinized Starch | 12.5 | 15.0 | 17.5 | 20.0 |
| 4. Cornstarch | 25.0 | 30.0 | 35.0 | 40.0 |
| 5. Modified Starch | 12.5 | 15.0 | 17.5 | 20.0 |
| 6. Magnesium Stearate | 4.0 | 5.0 | 6.0 | 7.0 |
| Total | 250 mg | 300 mg | 350 mg | 400 mg |

Procedure:
1. Mix items 1-5 in a suitable mixer, granulate with water. Dry overnight in an oven. Mill through a Fitzpatrick mill.
2. Mix with item 6 and compress on a suitable press.

EXAMPLE 34

Capsule Formulation

| | mg/capsule | | | |
|---|---|---|---|---|
| 1. 8-chloro-2-methyl-6-phenyl-4H-pyrazolo [1,5-a] [1,4] benzodiazepine | 1.0 | 5.0 | 10.0 | 50.0 |
| 2. Lactose | 149.0 | 182.5 | 215.0 | 250.0 |
| 3. Cornstarch | 40.0 | 50.0 | 60.0 | 80.0 |
| 4. Magnesium Stearate | 2.0 | 2.5 | 3.0 | 4.0 |
| 5. Talc | 8.0 | 10.0 | 12.0 | 16.0 |
| Total | 200 mg | 250 mg | 300 mg | 400 mg |

Procedure:
Mix items 1-3 in a suitable mixer. Mill through suitable mill.
2. Mix with items 4 and 5 and fill on capsule machine.

EXAMPLE 35

Direct Compression Tablet Formulation

| | mg/tablet | | | |
|---|---|---|---|---|
| 1. 8-chloro-2-methyl-6-phenyl-4H-pyrazolo [1,5-a] [1,4] benzodiazepine | 1.0 | 5.0 | 10.0 | 50.0 |
| 2. Lactose, Anhydrous DTG | 127.0 | 142.5 | 182.0 | 206.0 |
| 3. Microcrystalline Cellulose | 40.0 | 50.0 | 60.0 | 80.0 |
| 4. Modified Starch | 10.0 | 12.5 | 15.0 | 20.0 |
| 5. Cornstarch | 20.0 | 25.0 | 30.0 | 40.0 |
| 6. Magnesium Stearate | 2.0 | 2.5 | 3.0 | 4.0 |
| Total | 200 mg | 250 mg | 300 mg | 400 mg |

Procedure:
1. Mix items 1-5 in a suitable mixer for 1 to 15 minutes.
2. Add item 6 and mix for 5 minutes. Compress on a suitable press

EXAMPLE 36

Direct Compression Tablet Formulation

| | mg/tablet | | | |
|---|---|---|---|---|
| 1. 2-acetamido-8-nitro-6-phenyl-4H-pyrazolo [1,5-a] [1,4] benzodiazepine | 1.0 | 5.0 | 10.0 | 50.0 |
| 2. Lactose, Anhydrous DTG | 127.0 | 142.5 | 182.0 | 206.0 |
| 3. Microcrystalline Cellulose | 40.0 | 50.0 | 60.0 | 80.0 |
| 4. Modified Starch | 10.0 | 12.5 | 15.0 | 20.0 |
| 5. Cornstarch | 20.0 | 25.0 | 30.0 | 40.0 |
| 6. Magnesium Stearate | 2.0 | 2.5 | 3.0 | 4.0 |
| Total | 200 mg | 250 mg | 300 mg | 400 mg |

Procedure:
1. Mix items 1-5 in a suitable mixer for 1 to 15 minutes.
2. Add items 6 and mix for 5 minutes. Compress on a suitable press.

EXAMPLE 37

Capsule Formulation

| | mg/capsule | | | |
|---|---|---|---|---|
| 1. 2-acetamido-8-nitro-6-phenyl-4H-pyrazolo [1,5-a] [1,4] benzodiazepine | 1.0 | 5.0 | 10.0 | 50.0 |
| 2. Lactose | 149.0 | 182.5 | 215.0 | 250.0 |
| 3. Cornstarch | 40.0 | 50.0 | 60.0 | 80.0 |
| 4. Magnesium Stearate | 2.0 | 2.5 | 3.0 | 4.0 |
| 5. Talc | 8.0 | 10.0 | 12.0 | 16.0 |
| Total | 200 mg | 250 mg | 300 mg | 400 mg |

Procedure:
1. Mix items 1-3 in a suitable mixer. Mill through suitable mill.
2. Mix with items 4 and 5 and fill on capsule machine.

EXAMPLE 38

Wet Granulation Tablet Formulation

| | mg/tablet | | | |
|---|---|---|---|---|
| 1. 2-acetamido-8-nitro-6-phenyl-4H-pyrazolo [1,5-a] [1,4] benzodiazepine | 1.0 | 5.0 | 10.0 | 50.0 |
| 2. Lactose | 195.0 | 230.0 | 264.0 | 263.0 |
| 3. Pregelatinized Starch | 12.5 | 15.0 | 17.5 | 20.0 |
| 4. Cornstarch | 25.0 | 30.0 | 35.0 | 40.0 |
| 5. Modified Starch | 12.5 | 15.0 | 17.5 | 20.0 |
| 6. Magnesium Stearate | 4.0 | 5.0 | 6.0 | 7.0 |
| total | 250 mg | 300 mg | 350 mg | 400 mg |

Procedure:
1. Mix items 1-5 in a suitable mixer, granulate with water. Dry overnight in an oven. Mill through a Fitzpatrick mill.
2. Mix with item 6 and compress on a suitable press.

We claim:
1. A compound of the formula

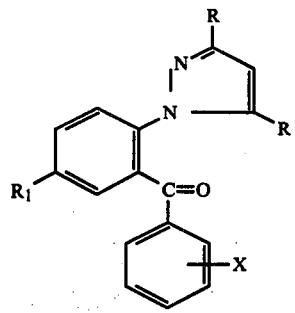

wherein X is hydrogen or halogen, $R_1$ is nitro, amino, hydrogen or halogen, and R is selected from the group consisting of $CO_2R_5$ and $CH_2OR_6$ wherein $R_5$ is lower alkyl and $R_6$ is acetyl.

2. A compound of the formula

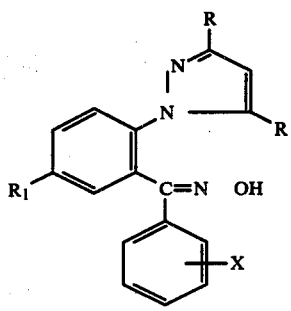

wherein X is hydrogen or halogen, $R_1$ is hydrogen or halogen and R is selected from the group consisting of $CO_2R_5$ and $CH_2OR_6$ wherein $R_5$ is lower alkyl and $R_6$ is acetyl.

3. A compound of the formula

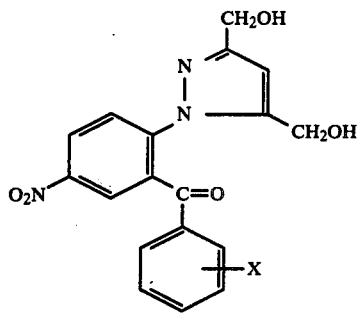

wherein X is hydrogen or halogen.

4. A compound of the formula

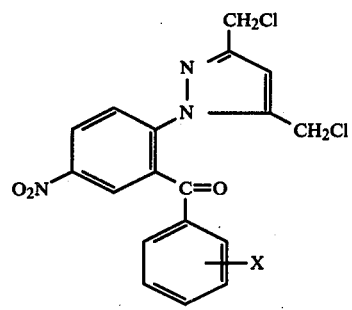

wherein X is hydrogen or halogen.

* * * * *

UNITED STATES PATENT AND TRADEMARK OFFICE
CERTIFICATE OF CORRECTION

PATENT NO. : 4,153,799
DATED : May 8, 1979
INVENTOR(S) : Norman Gilman and Rodney I. Fryer It is certified that error appears in the above–identified patent and that said Letters Patent are hereby corrected as shown below:

Claim 2, column 29, line 26, C=N  OH, should be: C=N~OH

Signed and Sealed this

Fifth Day of February 1980

[SEAL]

Attest:

SIDNEY A. DIAMOND

Attesting Officer

Commissioner of Patents and Trademarks